United States Patent
Minisci et al.

(10) Patent No.: US 8,445,729 B2
(45) Date of Patent: *May 21, 2013

(54) PROCESS FOR THE PRODUCTION OF ALKYLBENZENE HYDROPEROXIDES UNDER MILD CONDITIONS AND IN THE PRESENCE OF NEW CATALYTIC SYSTEMS

(75) Inventors: Francesco Minisci, Milan (IT); Ombretta Porta, Milan (IT); Angelo Clerici, legal representative, Milan (IT); Alberto Clerici, legal representative, Milan (IT); Carlo Punta, Milan (IT); Francesco Recupero, Milan (IT); Cristian Gambarotti, Cremona (IT); Raffaele Spaccini, Papiano (IT)

(73) Assignee: Polimeri Europa S.p.A., San Donato Milanese (IT)

( * ) Notice: Subject to any disclaimer, the term of this patent is extended or adjusted under 35 U.S.C. 154(b) by 100 days.

This patent is subject to a terminal disclaimer.

(21) Appl. No.: 12/933,204

(22) PCT Filed: Mar. 13, 2009

(86) PCT No.: PCT/EP2009/001922
§ 371 (c)(1),
(2), (4) Date: Nov. 9, 2010

(87) PCT Pub. No.: WO2009/115276
PCT Pub. Date: Sep. 24, 2009

(65) Prior Publication Data
US 2011/0251436 A1    Oct. 13, 2011

(30) Foreign Application Priority Data
Mar. 18, 2008 (IT) ................................ MI2008A0461

(51) Int. Cl.
*C07C 409/00* (2006.01)

(52) U.S. Cl.
USPC ............ 568/573; 568/558; 568/569; 568/570

(58) Field of Classification Search ........................ None
See application file for complete search history.

(56) References Cited

U.S. PATENT DOCUMENTS 6,720,462 B2 * 4/2004 Duda et al. .................... 568/768
2010/0234589 A1 * 9/2010 Dakka et al. .................. 540/534

FOREIGN PATENT DOCUMENTS
WO    2008 037435    4/2008

OTHER PUBLICATIONS

Fukuda, Osamu et al., "Preparation of Hydroperoxides by N-Hydroxyphthalimide-Catalyzed Aerobic Oxidation of Alkylbenzenes and Hydroaromatic Compounds and Its Application", Advanced Synthesis & Catalysis, vol. 343, No. 8, pp. 809-813, XP002432348, ISSN: 1615-4150. (Jan. 1, 2001).
Sugamoto, Kazuhiro et al. "Regioselective Hydroperoxygenation of Aralkanes and α, β-Unsaturated Carbonyl Compounds Catalyzed by N-Hydroxyphthalimide and 2,2'-Azobis (4-methoxy-2,4-dimethylvaleronitrile)", Synthetic Communications, vol. 35, pp. 1865-1874, XP009120109, ISSN: 0039-7911, (2005).
Sheldon, A. Roger et al., "Organocatalytic Oxidations Mediated by Nitroxyl Radicals", Advanced Synthesis & Catalysis, vol. 346, pp. 1051-1071, XP002459137, ISSN: 1615-4169, (Jan. 1, 2004).
U.S. Appl. No. 12/933,190, filed Sep. 17, 2010, Minisci, et al.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

Process for the preparation of hydroperoxides of alkylbenzenes characterized by the fact that the alkylbenzene reacts with oxygen in the presence of a catalytic system which includes an N-hydroxyimide or an N-hydroxysulfamide and a polar solvent.

20 Claims, No Drawings

PROCESS FOR THE PRODUCTION OF ALKYLBENZENE HYDROPEROXIDES UNDER MILD CONDITIONS AND IN THE PRESENCE OF NEW CATALYTIC SYSTEMS

FIELD OF THE INVENTION

The present invention concerns a process for the production of hydroperoxides of alkylbenzenes under mild conditions and in the presence of a new catalytic system.

Alkylbenzene hydroperoxides are useful intermediates for the production of phenol and a variety of ketones of relevant interest (acetone, methylethylketone, cyclohexanone) by the aerobic oxidation of alkylbenzenes such as isopropyl-, cyclohexyl- and sec-butyl-benzenes, which can be easily obtained by the alkylation of benzene with the corresponding alkenes (propene, butene, cyclohexene, cyclo-octene and cyclododecene).

ART PRIOR TO THE INVENTION

The industrial production of phenol is based on the Hock process, which involves the autoxidation of cumene to the corresponding hydroperoxide and its subsequent acid-catalyzed decomposition to phenol and acetone (Ullman's Encyclopedia of Industrial Organic Chemicals, Vol. A9, 1958, 225, Wiley-VCH). The most complex phase which mainly affects the whole process is the autoxidation, in which the hydroperoxide formed acts as initiator of the radical chain by decomposition to cumyloxyl radical. The latter can form cumyl alcohol by the hydrogen abstraction from cumene or undergoes β-scission giving acetophenone and methyl radical. These aspects determine various drawbacks which influence the whole process. The selectivity in hydroperoxide formation decreases to the extent in which the hydroperoxide itself acts as initiator. On the other hand, the hydroperoxide decomposition increases with the conversion and temperature. A high conversion causes a higher concentration of hydroperoxide and therefore a greater decomposition and a lower selectivity. Furthermore, the methyl radical, formed in the β-scission of the cumyloxyl radical, is oxidized under the reaction conditions to formic acid. The latter catalyzes the decomposition of the hydroperoxide to phenol, which inhibits the oxidation process. In industrial processes, formic acid therefore creates the necessity of operating in the presence of a base, to neutralize the carboxylic acid.

In order to eliminate or reduce these disadvantages, various expedients have been taken into consideration, such as the use of suitable metallic complexes as catalysts or co-catalysts, which increase the conversion rate and allow to work at lower temperatures at which the hydroperoxide is more stable (Ishii, Y. at al. J. Mol. Catalysis A, 1987, 117, 123). The higher thermal stability of the hydroperoxides at low temperatures, however, is negatively balanced by the redox decomposition caused by the metallic salts. These catalytic systems have consequently proved to be inadequate for the preparation of hydroperoxides whereas they are of great industrial interest for the preparation of other oxygenated products (alcohols, aldehydes, ketones, carboxylic acids).

Recently, new catalytic systems have been proposed for the aerobic oxidation of cumene and other alkylbenzenes, based upon the use of N-hydroxyimides and sulfamides associated to radical initiators, such as peroxides and azo-derivatives, which operate without metallic salts (Ishii, Y. at al. Adv. Synth. Catal. 2001, 343, 809 and 2004, 346, 199; Sheldon, R. A. at al. Adv. Synth. Catal. 2004, 346, 1051; Levin, D. at al. WO 2007/073916 A1; U.S. Pat. Nos. 6,852,893; 6,720,462).

N-hydroxyphthalimide, which can be easily obtained from cheap industrial products (phthalic anhydride and hydroxyl amine) is of particular interest. The catalytic activity (Minisci, F. et al. J. Mol. Catal. A, 2003, 63, 204 and 2006, 251, 129; Recupero, F. and Punta C., Chem. Rev. 2007, 107, 3800-3842) is related to the higher rate of hydrogen abstraction from cumene by means of the nitroxide radical (3,25 $M^{-1}s^{-1}$ at 25° C.), generated in the catalytic cycle from the N-hydroxyphthalimide, with respect to rate of hydrogen abstraction from cumene by cumylperoxyl radical (0,18 $M^{-1}s^{-1}$ at 25° C.), involved in the non-catalyzed chain process.

In the presence of N-hydroxyphthalimide, peracids and dioxyranes proved to have a considerable activity for the production of cumene hydroperoxide under mild aerobic conditions, with a high conversion and selectivity. (Minisci et al. PCT/EP07/008341).

The behaviour of peracids and dioxyranes is not correlated to the classic initiators (Adv, Synth. Catal. 2001, 343, 809 and Adv, Synth. Catal. 2004, 346, 1051; U.S. Pat. No. 6,720,462), in which their thermal decomposition produces radicals which initiate the autoxidative chain catalyzed by N-hydroxy-derivatives. The peracids and the dioxyranes are stable at the operating temperatures. In the presence of N-hydroxy-derivatives, they form nitroxide radicals by means of an induced homolysis mechanism (Minisci, F. et al. Tetrahedron Lett. 2006, 47, 1421).

The use of N-hydroxy-derivatives presents undoubted advantages with respect to non-catalyzed autoxidations, but also various disadvantages deriving from the decomposition of the initiators.

The Applicants have recently found that N-hydroxyphthalimide can catalyze the peroxidation of cumene under mild conditions if the aerobic oxidation is carried out in the presence of a moderate quantity of polar solvent (ketones, nitriles, esters, dialkyl carbonates and tertiary alcohols) which are completely stable under operative conditions. Under these conditions, the oxygen itself initiates the chain radical process, which leads to the formation or hydroperoxide, generating the corresponding nitroxide radical from the N-hydroxy-derivative. Under the same operating conditions, in the absence of N-hydroxy-derivative, there is no significant reaction.

The selectivity of this process to hydroperoxide is extremely high (about 99%) and there is no formation of by-products deriving from the radical initiator (not present in this system) or from the decomposition of the cumene hydroperoxide or N-hydroxy-derivative. The catalyst remains unaltered and can be easily recovered at the end of the reaction by means of crystallization and extraction with water. The cost incidence of the catalyst on the overall process is therefore negligible.

Under the same operating conditions, in the absence of polar solvents, there is no significant oxidation.

The oxidation of cumene at 125° C., catalyzed by N-hydroxyphthalimide in the presence of cumyl hydroperoxide, takes place with a high conversion also without polar solvents but the selectivity to hydroperoxide is <70% and the catalyst decomposition is observed. This result is in contrast with what is indicated in a recent patent (U.S. Pat. No. 6,852,893 B2) which claims a selectivity of 99.9% to hydroperoxide under the same conditions, whereas no mention is made with respect to the destiny of the catalyst. Repeated experiments in an attempt to reproduce the example provided in this patent have always led to a selectivity of hydroperoxide <70% and to the destruction of the catalyst. In the sole example included in U.S. Pat. No. 6,852,893 B2, on the other hand, the analysis method of cumene hydroperoxide is not indicated.

The analytical method described in this document, in order to know the selectivity to hydroperoxide and to verify the destiny of the catalyst, is based on $^1$H NMR measurements effected on the reaction mixture, comparing the obtained results with pure samples of cumene hydroperoxide and N-hydroxyphthalimide. The selectivity to hydroperoxide was further confirmed by means of iodometric titration.

In the peroxidation of cumene, acetone is the most advantageous among polar solvents as it is obtained as co-product during the acid decomposition of the hydroperoxide to phenol.

The demand for phenol however is constantly growing with respect to that for acetone. There is consequently a growing interest in processes for the production of phenol which avoid the formation of acetone. In particular, the peroxidation of sec-butylbenzene is interesting as the cost of propylene, widely used for the production of polypropylene and propylene oxide, with respect to that of butanes, is continuously increasing and the offer is lower than the market request. Furthermore, the methyl ethyl ketone obtained together with phenol from the peroxidation process of sec-butylbenzene, is widely used as solvent in the chemical industry.

Cyclo-alkylbenzenes, which can be easily obtained by the alkylation of benzene with cyclo-alkenes, are also compounds of interest which lead to peroxidation processes by the method object of the present invention. The corresponding cyclo-alkanones, obtained together with phenol, are of great industrial interest for the production of lactones and dicarboxylic acids.

Thus, object of the present invention, described in the enclosed claims, is the preparation of peroxides of alkylbenzenes, such as isopropyl-, sec-butyl-, cycloalkyl-benzenes, by the aerobic oxidation of the same in the presence of a catalytic system, which includes N-hydroxyimides or N-hydroxysulfamides, associated with a polar solvent. The temperature does not exceed 120° C. and preferably ranges from 50 to 100° C. The polar, solvent can be a ketone, also the same deriving from the acid decomposition of the hydroperoxide (acetone, methyl ethylketone, cyclohexanone) or other solvents such as nitriles, esters, tertiary alcohols, dialkyl carbonates, also stable under the reaction conditions.

The quantity of N-hydroxy-derivative catalyst preferably ranges from 0.5 to 10% in moles.

The ratio between the volume of polar solvent with respect to the volume of alkylbenzene preferably varies within the range of 1:1 and 1:10.

The N-hydroxy-derivative, in particular the more convenient N-hydroxyphthalimide, at the end of the reaction, is mostly recovered by crystallization from the reaction mixture from which the polar solvent has been removed by distillation . The small quantity of residual catalyst is recovered by extraction with water of the reaction mixture.

Under the same conditions, in the absence of both N-hydroxyphthalimide and the polar solvent, there is no significant oxidation reaction.

The following examples are provided for illustrative purposes but without representing any limit for the process of the present invention.

EXAMPLE 1

A solution of 20 mL of cumene (144 mmoles), 7.5 mL of acetone and 1.44 mmoles of N-hydroxyphthalimide is stirred at 65° C. for 24 hours under an oxygen atmosphere of a pressure of 1 bar. $^1$H-NMR analysis of the reaction mixture showed a cumene conversion of 35% with a selectivity of cumyl hydroperoxide of 99% without a substantial decomposition of the N-hydroxyphthalimide. The acetone was removed by distillation and 1.29 mmoles of N-hydroxyphthalimide crystallized by cooling. A further 0.03 mmoles of N-hydroxyphthalimide were recovered by extraction with water.

EXAMPLE 2

The same procedure was adopted as in Example 1, using a solution of 3.6 mmoles of N-hydroxyphthalimide in 10 mL of cumene and 10 mL of acetone at 58° C. $^1$H-NMR analysis of the reaction mixture showed a cumene conversion of 37% with a selectivity in cumyl hydroperoxide of 99%. 3.2 mmoles of N-hydroxyphthalimide were recovered.

EXAMPLE 3

The same procedure was adopted as in Example 1, using 7.5 mL of acetonitrile at 70° C. instead of acetone. $^1$H-NMR analysis of the reaction mixture showed a cumene conversion of 48% with a selectivity in cumyl hydroperoxide of 99% (result confirmed by iodometric titration). 1.31 mmoles of N-hydroxyphthalimide were recovered.

EXAMPLE 4

The same procedure was adopted as in Example 1, using a solution of 0.7 mmoles of N-hydroxyphthalimide in 10 mL of cumene and 3.7 mL of 2-pentanone at 100° C. for 6 hours. $^1$H-NMR analysis of the reaction mixture showed a cumene conversion of 39% with a selectivity in cumyl hydroperoxide of 99%. 0.64 mmoles of N-hydroxyphtrialimide were recovered.

EXAMPLE 5

The same procedure was adopted as in Example 1, in the absence of N-hydroxyphthalimide. There is no significant conversion of the cumene.

EXAMPLE 6

The same procedure was adopted as in Example 1, in the absence of acetone. The cumene conversion is <1%.

EXAMPLE 7

A solution of 10 mL of cumene (72 mmoles), 1.44 mL of cumyl hydroperoxide and 0.72 mmoles of N-hydroxyphthalimide is stirred at 125° C. for 6 hours in under an oxygen atmosphere of 1 bar. $^1$H-NMR analysis of the reaction mixture showed a cumene conversion of 63% with a selectivity in cumyl hydroperoxide of 68% (result confirmed by iodometric titration). The main by-product is cumyl alcohol and the secondary products are acetophenone and dicumyl peroxide. The N-hydroxyphthalimide is mostly decomposed.

EXAMPLE 8

A solution of 10 mL of sec-butylbenzene (64.3 mmoles), 3.75 mL of acetonitrile and 0.64 mmoles of N-hydroxyphthalimide is stirred at 70° C. for 24 hours in an atmosphere of oxygen at a pressure of 1 bar. $^1$H-NMR analysis of the reaction mixture showed a secbutylbenzene conversion of 20% with a selectivity in sec-butyl hydroperoxide of 89% (result confirmed by iodometric titration) and 11% of acetophenone. The acetonitrile is removed by distillation and 0.57 mmoles of N-hydroxyphthalimide are recovered.

EXAMPLE 9

A solution of 10 mL of phenyl cyclohexane (58.8 mmoles), 3.75 mL of acetonitrile and 0.58 mmoles of N-hydroxyphthalimide is stirred at 70° C. for 24 hours in an atmosphere of oxygen at a pressure of 1 bar. $^1$H-NMR analysis of the reaction mixture showed a phenylcyclohexane conversion of 14% with a selectivity to 1-phenyl cyclohexyl hydroperoxide of 100% (result confirmed by iodometric titration and GC-MS analysis in the presence of an internal standard after reduction of the hydroperoxide to the corresponding alcohol with PPh$_3$). There is no decomposition of the N-hydroxyphthalimide. The acetonitrile is removed by distillation and 0.52 mmoles of N-hydroxyphthalimide are recovered.

EXAMPLE 10

The same procedure was adopted as in Example 8, in the absence of acetonitrile. There is no significant conversion of the sec-butylbenzene.

EXAMPLE 11

The same procedure was adopted as in Example 9, in the absence of acetonitrile. There is no significant conversion of the phenyl cyclohexane.

The invention claimed is:

1. A process for preparing at least one hydroperoxide of at least one alkylbenzene, comprising
reacting the alkylbenzene with oxygen in the presence of a catalytic system including an N-hydroxyimide or an N-hydroxysulfamide and a polar solvent, in a reaction mixture, in the absence of a radical initiator;
wherein a ratio between a volume of the polar solvent with respect to a volume of the alkylbenzene is from 5:1 to 1:20.

2. The process according to claim 1, wherein the alkylbenzene is at least one selected from the group consisting of isopropyl-, sec-butyl-, cyclohexyl-, cyclo-octyl-, and cyclododecyl-benzenes.

3. The process according to claim 1, wherein N-hydroxyphthalimide and N-hydroxy saccharine are catalysts.

4. The process according to claim 1, wherein the reaction temperature does not exceed 120° C.

5. The process according to claim 1, wherein the reaction is carried out with oxygen or air at a pressure of 1-20 bar.

6. The process according to claim 4, wherein the reaction is carried out at a temperature ranging from 50 to 100° C.

7. The process according to claim 1, wherein the polar solvent is at least one selected from the group consisting of ketones, nitriles, esters, tertiary alcohols, and dialkyl carbonates.

8. The process according to claim 1, wherein the polar solvent is acetone when the alkylbenzene is isopropylbenzene (cumene).

9. The process according to claim 1, wherein the polar solvent is methyl ethyl ketone when the alkylbenzene is sec-butylbenzene.

10. The process according to claim 1, wherein the polar solvent is cyclohexanone when the alkylbenzene is phenylcyclohexane.

11. The process according to claim 1, further comprising recovering the catalyst by separation from the polar solvent and crystallizing from the reaction mixture.

12. The process according to claim 1, further comprising recovering the catalyst by extraction with water.

13. The process according to claim 1, wherein a quantity of catalyst N-hydroxyimide or N-hydroxysulfamide ranges from 0.1 to 10% in moles with respect to the alkylbenzene.

14. The process according to claim 2, wherein the polar solvent is acetone when the alkylbenzene is isopropylberizene(cumene).

15. The process according to claim 2, wherein the polar solvent is methyl ethyl ketone when the alkylbenzene is sec-butylbenzene.

16. The process according to claim 2, wherein the polar solvent is cyclohexanone when the alkylbenzene is phenylcyclohexane.

17. The process according to claim 2, further comprising recovering the catalyst by separation from the polar solvent and crystallizing from the reaction mixture.

18. The process according to claim 3, further comprising recovering the catalyst by separation from the polar solvent and crystallizing from the reaction mixture.

19. The process according to claim 2, further comprising recovering the catalyst by extraction with water.

20. The process according to claim 1, wherein the catalytic system consist of the N-hydroxyimide or an N-hydroxysulfamide and the polar solvent.

* * * * *